United States Patent [19]

Barbelet et al.

[11] 4,282,072
[45] Aug. 4, 1981

[54] METHOD FOR AUTOMATIC INDUSTRIAL ELECTROCHEMICAL ANALYSIS

[75] Inventors: Michel Barbelet, Lyons; Jean-Pierre Caujolle, Ste Foy les Lyon; Claude Scramoncin, St Priest; Edmond Thibault, Saint Chamond, all of France

[73] Assignee: ELF France, Paris, France

[21] Appl. No.: 75,998

[22] Filed: Sep. 17, 1979

[30] Foreign Application Priority Data

Sep. 18, 1978 [FR] France .............................. 78 26653

[51] Int. Cl.³ ........................................... G01N 27/42
[52] U.S. Cl. ................................. 204/1 T; 204/195 T
[58] Field of Search ........................ 204/195 T, 1 M

[56] References Cited

U.S. PATENT DOCUMENTS 2,928,774  3/1960  Leisey .................. 204/195 T X
4,018,565  4/1977  Fletcher et al. .......... 204/195 T X Primary Examiner—G. L. Kaplan
Attorney, Agent, or Firm—Burgess, Ryan and Wayne

[57] ABSTRACT

A method for automatic electrochemical titration, by argentimetric coulometry, comprising automatic injection into an electrochemical cell of a sample containing a substance A to be titrated, and an electrolyte, the ratio of sample to electrolyte being constant, and coulometrically titrating the mixture by producing a substance B, at an electrode and following the reaction between A and B, by potentiometry. The method is particularly useful for the automatic, industrial analysis of mercaptans.

5 Claims, 1 Drawing Figure

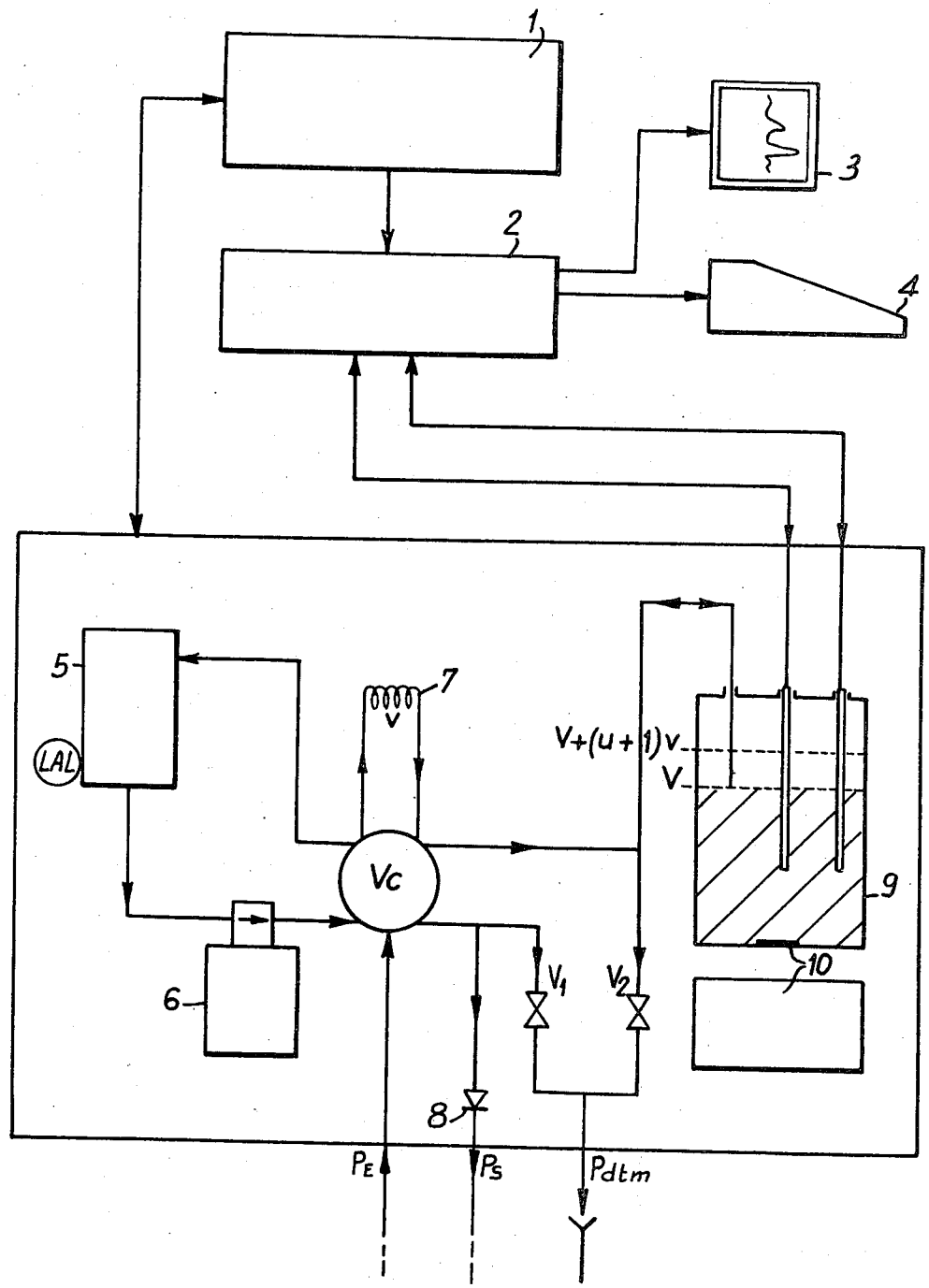

METHOD FOR AUTOMATIC INDUSTRIAL ELECTROCHEMICAL ANALYSIS

BACKGROUND OF THE INVENTION

Essential data for the automatic operation of a unit for sweetening kerosene or certain petroleum cuts, is the knowledge of their mercaptan sulfur content. More precisely, it is necessary to know the mercaptan content of the feed entering the unit, in order to adjust the air flow necessary for oxidation in the reactor, and the mercaptan content of the product at the outlet of the unit in order to meet specifications.

The object of the invention is, therefore, to provide a method and an apparatus for automatic titration of mercaptans, in an industrial sweetener unti for petroleum cuts.

Among the methods used in the laboratory, the argentimetric method consists in titrating the mercaptans by silver salts, and running a potentiometric detection of the end of the titration, according to the reaction:

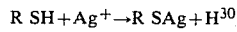

$$R\,SH + Ag^+ \rightarrow R\,SAg + H^{30}$$

A variation of this titration, which is of particular interest with a view to automation, is the coulometric generation of the $Ag^+$ ion in the electrolyte solution by anodic oxidation of a metal silver gauze. The number of coulombs necessary for the titration is proportional to the quantity of mercaptans originally present in the solution.

Coulometric titration lends itself well to automation and since it requires no preparation of a reagent, it is not limited by the range of concentration of the mercaptans, and their molecular mass is not a factor. The precision is high. The titration times with a pilot-operated coulometer are short.

BRIEF SUMMARY OF THE INVENTION

The method of electrochemical titration which is the object of the invention, comprises an automated titration by argentimetric coulometry, characterized by automatic injection of the substance to be titrated and the electrolyte.

The operational principal developed is as follows:

A predetermined volume of kerosene v, defined by a sampling loop, is pushed by a predetermined volume v' of electrolyte into the titration cell. The mixture of electrolyte and kerosene is received in the titration cell containing a volume V of the mixture in the same ratio $u=v'/v$, which served for the preceding titration, hence at the potential of equivalence. The titration comprises generating the quantity of $Ag^+$ which reacts exactly with the quantity of mercaptans just injected.

This method of operation insures identical conditions for titrations, and satisfactory repeatability.

DETAILED DESCRIPTION OF THE INVENTION

The device for carrying out the invention, represented in FIG. 1, comprises the following:

A control unit (programmable automatic unit) 1
A pilot-operated coulometer 2
A recorder 3
A printout 4
An electrolyte reserve 5
A proportioning pump 6
A chromatography-type valve −8 channels—2 positions (Vc)
A sampling loop 7
A non-return flap valve 8
Automatic 2-way valves ($V_1$, $V_2$)
A complete coulometric cell 9 with magnetic agitator 10.

The cyclic operation of the device described is controlled by the programmable automatic control unit. Each analysis is broken down into 4 phases which are summarized in Table 1.

METHOD OF OPERATION

A method of operation which minimizes the consumption of electrolyte is as follows:

At the start, the coulometric cell contains a volume $V=300$ cc of a mixture of electrolyte plus kerosene, in the ratio $u=2$ (electrolyte/kerosene)

100 cc of kerosene
200 cc of electrolyte of composition:
—3.25 g of ammonium nitrate ppa
—15 cc of concentrated ammonia ppa
—1000 cc of absolute ethanol ppa The electrode pairs used are:

A silver electrode and a counter-electrode of platinum for generation of the $Ag^+$ ions;

An $Ag/Ag_2S$ indicator electrode and a reference electrode of mercurous sulfate, for detection.

By generation of $Ag^+$ ions, the volume V is brought to the potential of equivalence (−550 mV relative to the reference electrode).

The cell is then ready to run titrations.

The programmable automatic control unit causes, at the time of each analysis, the injection of a predetermined volume v of kerosene, the volume determined as a function of the sulfur mercaptan content (for example, $v=10$ ml for S (RSH) in the vicinity of 10 mg/kg) and a volume $v'=u\,v$ of electrolyte. The total volume in the cell is then equal to $V+(u+1)\,v$ and the ratio of electrolyte to kerosene is kept at the value $u=2$.

The kerosene circuit is represented in the diagram in FIG. 1—$P_E$ and $P_s$ indicate the input and output pressures of the kerosene.

The titration is then completed, and the result printed out.

Next, the draining phase permits the evacuation of a volume $(u+1)\,v$ of the neutralized reaction mixture, which is represented in FIG. 1 by Patm.

Note that $P_E$ is higher than $P_s$ which in turn is higher than atmospheric pressure.

The volume in the cell is thus reduced to the initial value $V=300$ cc. The ratio of electrolyte to kerosene remains constant and equal to 2.

This method of operation insures identical successive titration conditions. Long-term tests have been made on kerosenes with different mercaptan contents. The results obtained are precise, repeatable, and not sensitive to the temperature, within a range of 5 to 40 degrees Celsius.

The consumption of electrolyte is low. The equipment is very dependable, and the automatic unit allows the correction of certain malfunctions (for example: resumption of analyses after current failures).

This method can, of course, be applied to any electrochemical titration requiring automation.

TABLE I

| PHASES | POSITION OF VALVES | | REMARKS |
|---|---|---|---|
| 1 - "STAND-BY" | $V_c$ | Position 1 | Electrolyte is kept in circulation on itself by means of proportioning pump |
|  | $V_1$ | Closed | Kerosene circulates in sampling loop under influence of pressure differential between entry and output |
|  | $V_2$ | Closed |  |
| 2 - "INJECTION" | $V_c$ | Position 2 | Cutoff of circulation of electrolyte on itself |
|  | $V_1$ | } Closed | Cutoff of kerosene purge of sampling loop |
|  | $V_2$ |  | Admission to cell of volumes v of kerosene and v' of electrolyte by means of proportioning pump |
| 3 - "RINSE" | $V_c$ | Position 1 | Electrolyte returned to circulation on itself |
|  | $V_1$ | Open only during rinse time | Sampling loop rinsed with kerosene toward the drain for a certain time |
|  | $V_2$ | Closed | After rinsing, the sampling loop is repurged by kerosene as in phase no. 1 |
| 3.2 - "TITRATION" |  |  | Simultaneous actuation of coulometer |
| 4 - "DRAINAGE OF CELL" | $V_c$ | Position 1 | Drainage of a volume $v + v'$ by means of a self-priming siphon |
|  | $V_1$ | Closed |  |
|  | $V_2$ | Open | (Starting conditions have thus been reached once again) |

We claim:

1. A method for automatic titration of a plurality of samples by argentimetric coulometry which comprises: automatically introducing a predetermined volume v of a sample, containing a substance A to be titrated, and a predetermined volume uv of an electrolyte, into a coulometric titration zone containing a known volume V of a mixture of electrolyte and sample at the potential of equivalence, said volume V being left over from a prior sample, and wherein the reaction volume held in the titration zone is equal to $V + (u+1)v$, the ratio of sample to electrolyte equal to u; coulometrically titrating the sample in the titration zone by producing a determined quantity of substance B and following the reaction between substances A and B by potentiometry wherein A is the substance in the sample whose quantity is to be determined and B is the substance which reacts with A which is generated in the coulometric titration zone and repeating said titration a plurality of times, wherein said volume V remains substantially constant from sample to sample.

2. The method of claim 1 wherein, after titration, a portion of the mixture in the titration zone is automatically discharged.

3. The method of claim 2, wherein, in the automatic discharge phase, the volume $V + (u+1)v$ of the mixture of electrolyte and sample in the ratio u, and containing neither A nor B in the free state, is reduced to the original volume V.

4. The method of claim 1, 2 or 3 wherein the steps of the process are determined by a logic control unit.

5. The method of claims 1, 2 or 3 wherein substance A is a mercaptan.

* * * * *

UNITED STATES PATENT AND TRADEMARK OFFICE
CERTIFICATE OF CORRECTION

PATENT NO. : 4,282,072

DATED : August 4, 1981

INVENTOR(S) : Barbelet, et al

It is certified that error appears in the above—identified patent and that said Letters Patent is hereby corrected as shown below:

Column 1, line 24: "$R\ SH + Ag^+ \rightarrow R\ SAg + H^{30}$" should read

--$R\ SH + Ag^+ \rightarrow R\ SAg + H^+$ --.

Signed and Sealed this

Ninth Day of February 1982

[SEAL]

Attest:

GERALD J. MOSSINGHOFF

Attesting Officer    Commissioner of Patents and Trademarks